United States Patent [19]

Wong et al.

[11] Patent Number: 5,758,643
[45] Date of Patent: Jun. 2, 1998

[54] METHOD AND APPARATUS FOR MONITORING BLOOD CHEMISTRY

[75] Inventors: David K. Wong, Del Mar; James E. Gharib, San Diego; Kenneth Curry, Oceanside; Luis Retana, San Diego, all of Calif.

[73] Assignee: Via Medical Corporation, San Diego, Calif.

[21] Appl. No.: 688,153

[22] Filed: Jul. 29, 1996

[51] Int. Cl.$^6$ .................................................. H61B 5/14
[52] U.S. Cl. ............................ 128/632; 128/760; 604/4
[58] Field of Search ................................ 128/632, 635, 128/760; 604/4; 204/403, 409, 411

[56] References Cited

U.S. PATENT DOCUMENTS

| | | | |
|---|---|---|---|
| 3,838,682 | 10/1974 | Clark et al. | 128/2 G |
| 3,910,256 | 10/1975 | Clark et al. | 128/2 G |
| 4,231,366 | 11/1980 | Schael | 128/214 E |
| 4,535,786 | 8/1985 | Kater | 128/760 |
| 4,573,968 | 3/1986 | Parker | 604/67 |
| 4,657,529 | 4/1987 | Prince et al. | 604/6 |
| 4,841,974 | 6/1989 | Gumbrecht et al. | 128/635 |
| 5,109,850 | 5/1992 | Blanco et al. | 128/635 |
| 5,165,406 | 11/1992 | Wong | 128/635 |
| 5,178,603 | 1/1993 | Prince | 604/6 |
| 5,220,920 | 6/1993 | Gharib | 128/635 |
| 5,250,439 | 10/1993 | Musho et al. | 435/25 |
| 5,271,815 | 12/1993 | Wong | 204/153.12 |
| 5,330,634 | 7/1994 | Wong et al. | 204/409 |
| 5,505,828 | 4/1996 | Wong et al. | |

Primary Examiner—Jennifer Bahr
Assistant Examiner—Eric F. Winakur
Attorney, Agent, or Firm—Sheppard, Mullin Richter & Hampton; James R. Brueggemann

[57] ABSTRACT

An improved system is disclosed for monitoring a patient's blood chemistry, wherein the system intermittently draws blood samples from the patient into a special sensor assembly having a plurality of analytical sensors, each sensitive to a particular parameter of the blood. After signals produced by these various sensors have been read, the system reinfuses the blood samples back into the patient. Withdrawal of the successive samples to a desired, optimal position within the sensor assembly is achieved by monitoring signals produced by one or more of the analytical sensors, themselves. This allows a catheter that connects the sensor assembly to the patient to have a variable length and internal volume and obviates the need for a separate, dedicated sensor for detecting the arrival of the blood sample at the desired position.

38 Claims, 2 Drawing Sheets

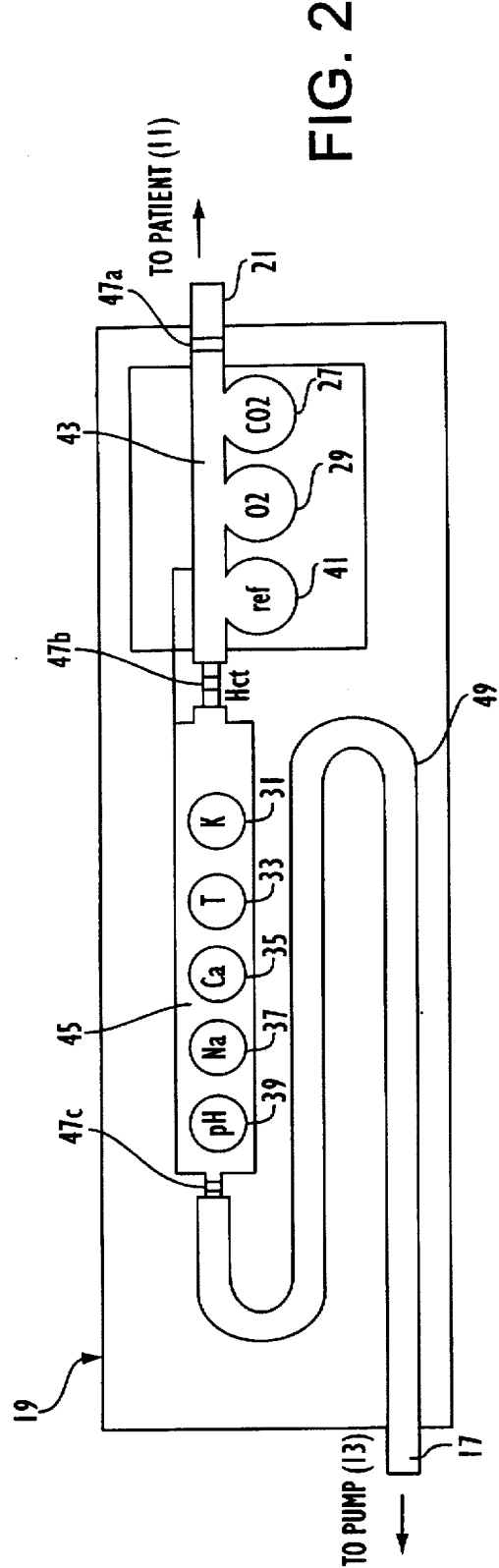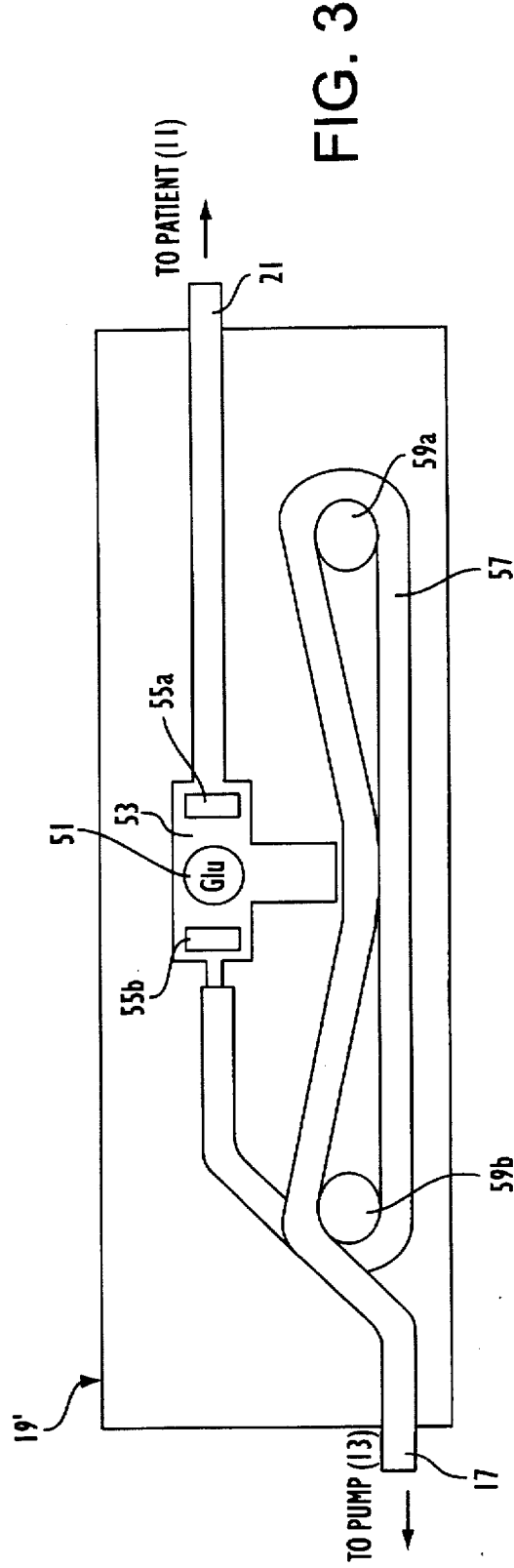

5,758,643

METHOD AND APPARATUS FOR MONITORING BLOOD CHEMISTRY

BACKGROUND OF THE INVENTION

This invention relates generally to methods and apparatus for monitoring a patient's blood chemistry and, more particularly, to methods and apparatus for controlling the withdrawal of a blood sample from a patient into a sensor assembly.

The invention is particularly suitable for use with a system that infuses an infusion fluid into a patient substantially continuously, with periodic interruptions for blood chemistry measurement. Such a system is described in U.S. Pat. No. 4,573,968. In that system, an infusion pump pumps a suitable infusion fluid via an infusion tube and catheter into a patient, but intermittently reverses its direction, to draw a sample of blood from the patient through the catheter and into a sensor assembly connected to the infusion tube. The physical configuration of one suitable sensor assembly is disclosed in U.S. Pat. No. 5,165,406. The sensor assembly includes a plurality of sensors that produce electrical signals corresponding to various conditions or parameters of the patient's blood. Examples of such parameters include concentrations of carbon dioxide, oxygen, potassium, calcium, and sodium, as well as hematocrit, temperature, and pH. These signals are supplied to a analyzer, which converts the signals into a form readable by a caregiver.

In systems of this kind, it is important that sufficient blood be drawn from the patient so that a true blood sample reaches all of the individual sensors of the sensor assembly. Determining the proper amount of blood to be drawn can be difficult, however, because the volume of liquid within the catheter can vary from case to case. It should, therefore, be appreciated that there is a need for an improved method and apparatus for precisely and repeatably controlling the drawing of a blood sample from a patient into a blood chemistry sensor assembly. The present invention fulfills this and other needs.

SUMMARY OF THE INVENTION

The present invention resides in an improved method and apparatus for precisely and repeatably controlling the drawing of a patient's blood sample to a prescribed position within a blood chemistry sensor assembly. The invention ensures that the blood sample reaches all of the sensor assembly's individual sensors and that sufficient additional blood is drawn to minimize the dilution effects of an adjacent infusion fluid. The invention has particular use as part of an infusion system that substantially continuously infuses an infusion fluid into patient, while intermittently reversing itself and drawing blood samples from the patient, for chemical analysis.

More particularly, the apparatus of the invention includes a reversible infusion pump that, under the control of a controller, normally pumps an infusion fluid in a forward direction from a fluid source into the patient via an infusion tube and a catheter. Intermittently, the controller operates the pump in a rearward direction, to draw a blood sample from the patient into the blood chemistry sensor assembly, which is connected to the infusion tube. The controller monitors the signal produced by a sensor of the sensor assembly, to detect the arrival of the blood at the sensor, after which time it ceases operating the pump in the rearward direction. The sensor signal then is monitored, to provide an indication of a predetermined parameter of the patient's blood.

In another, more detailed feature of the invention, the sensor whose signal is monitored in the detecting of the arrival of the patient's blood sample is selected from the group consisting of carbon dioxide sensors, oxygen sensors, potassium sensors, calcium sensors, sodium sensors, hematocrit sensors, temperature sensors, glucose sensors, and pH sensors. In a preferred form of the invention, the controller detects the arrival of the blood sample in response to a predetermined combination of signals generated by both a carbon dioxide sensor and a calcium sensor.

In another more detailed feature of the invention, the apparatus actuates an alarm in response to a predetermined signal received from one or more of the sensor assembly's sensors. An alarm also is actuated in response to a failure to detect the arrival of the blood sample within a predetermined time period after operation of the infusion pump in the rearward direction is initiated and in response to detecting the arrival of the blood sample at a time too soon after operation of the infusion pump in the rearward direction is initiated.

In yet another more detailed feature of the invention, the controller ceases operation of the infusion pump in the rearward direction a prescribed time after the arrival of the blood sample has been detected. Preferably, this occurs after a prescribed additional volume of blood has been drawn from the patient.

Other features and advantages of the invention should become apparent from the following description of the preferred embodiments, taken in conjunction with the accompanying drawings, which illustrate, by way of example, the principles of the invention.

BRIEF DESCRIPTION OF THE DRAWINGS

FIG. 2 is a plan view of a first blood chemistry sensor assembly suitable for use with the present invention, this sensor assembly including sensors indicative of the concentrations of carbon dioxide, oxygen, potassium, calcium, and sodium, as well as sensors indicative of hematocrit, temperature, and pH.

FIG. 3 is a plan view of a second blood chemistry sensor assembly suitable for use with the present invention, this sensor assembly including a sensor indicative of glucose concentration.

DESCRIPTION OF THE PREFERRED EMBODIMENTS

Figure 1:
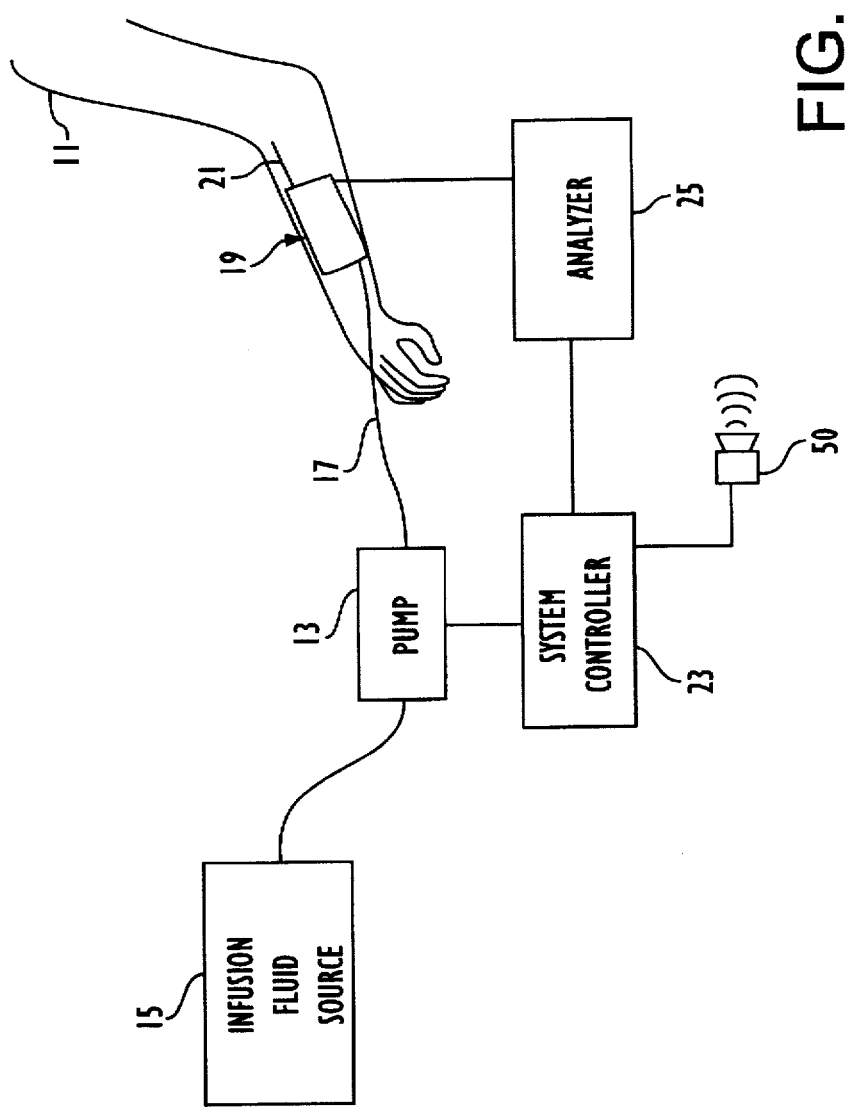
FIG. 1 is a diagrammatic illustration of an automated infusion and blood testing apparatus system suitable for use with the present invention.

With reference now to the drawings, for purposes of illustration, and particularly to FIG. 1, there is shown a system for infusing an infusion fluid into a patient 11 while intermittently monitoring a number of parameters of the patient's blood. The system includes an infusion pump 13 for pumping the infusion fluid in a forward direction from a source 15 to the patient, via an infusion tube 17, a blood chemistry sensor assembly 19, and a catheter 21. The infusion fluid preferably is a physiological isotonic saline solution of appropriate concentration, although the fluid also may incorporate selected nutrients or medications for delivery to the patient.

At appropriate times, a system controller 23 causes the infusion pump 13 to reverse its direction, and instead to draw blood from the patient 11 through the catheter 21 and into the sensor assembly 19. This reversal of the pump's direction may occur at predetermined time intervals, or upon receipt by the controller of a manual command issued by a caregiver.

One suitable blood chemistry sensor assembly 19 is depicted in FIG. 2. It includes a plurality of analytical sensors, each producing a signal indicative of a separate parameter of the adjacent fluid. Examples of such parameters include concentrations of carbon dioxide, oxygen, potassium, calcium, and sodium. Other parameters that can be sensed by such sensors include hematocrit, temperature, and pH.

To perform the desired analysis, a sample of the patient's blood must be drawn into a position where it contacts all of the analytical sensors of the sensor assembly 19. In addition, sufficient additional blood preferably is drawn to minimize the effects of any dilution of the blood by the adjacent infusion fluid.

After the patient's blood sample has been drawn to the appropriate position, electrical signals from the various analytical sensors are read and analyzed by an analyzer 25 (FIG. 1). Preferably, a brief stabilization period of about 8 seconds is allowed to elapse before the sensors are read. The analyzer converts the electrical signals from the sensors into corresponding indications of the concentrations of one or more components, or of other parameters, of the patient's blood. These indications can be read by a caregiver monitoring the patient.

Thereafter, after the analysis has been completed, the controller 23 again operates the pump 13 in its forward direction, to flush the blood sample out of the sensor assembly 19 and back into the patient 11. Pumping of the infusion fluid into the patient then resumes. This pumping can occur at a relatively low flow rate of about 1 to 10 milliliters per hour.

When the infusion pump 13 is operated in its rearward direction, it draws the patient's blood at a substantially constant flow rate. However, because the length and internal volume of the catheter 21 located between the sensor assembly 19 and the patient 11 can vary, merely drawing the blood for a fixed time duration cannot ensure that the blood will reach its desired position in the sensor assembly. Some means for sensing the arrival of the blood sample at its desired position, therefore, is required. If necessary, a dedicated sensor could be provided within the sensor assembly, for sensing the arrival of the blood sample at its desired position. However, such a dedicated sensor would add expense and complexity to the sensor assembly.

According to the invention, the need for such a dedicated sensor within the sensor assembly 19, for detecting the arrival of the blood sample at its desired position within the assembly, is obviated by configuring the controller 23 to monitor the signal from one or more of the analytical sensors that already are present within the assembly. In response to detecting a predetermined signal or change in signal from the sensor or sensors being monitored, the controller ceases operating the pump in the rearward direction.

As mentioned above, an additional amount of blood is drawn from the patient 11 after the sample first reaches the analytical sensor being monitored, to minimize the dilution effects of the adjacent infusion fluid. Although several milliliters would be required to completely eliminate any such dilution effects, the effects can be reduced to an acceptably small, and repeatable, level by drawing merely about 0.1–1.0 milliliters of additional blood after the blood has been detected to have arrived at the sensor being monitored. The controller 23, therefore, is programmed to continue drawing blood for whatever time duration is required after detecting the arrival of the blood sample at the sensor before switching off the pump 13.

Additionally, the controller 23 preferably is programmed to actuate an alarm and to switch off the infusion pump 13 if the arrival of the patient's blood sample has not been detected within a predetermined maximum time duration following initiation of pump's reversal and also if the arrival is detected to have occurred before a predetermined minimum time duration. This ensures that the pump is not operated indefinitely to draw blood from the patient in case of a sensor failure or other system failure, and it also ensures that the caregiver is alerted to a possible sensor failure, a blockage in the infusion tube 17 or catheter 21, or other system failure.

With reference again to FIG. 2, there is shown a first embodiment of a blood chemistry sensor assembly 19 that can be incorporated into the system of the invention. The sensor assembly is depicted to include a number of analytical sensors, including a carbon dioxide sensor 27, an oxygen sensor 29, a potassium sensor 31, a thermistor 33, a calcium sensor 35, a sodium sensor 37, and a pH sensor 39. Each sensor produces an electrical signal indicative of the concentrations of a particular component, or of another parameter of whatever fluid is located adjacent to it. The carbon dioxide sensor and the oxygen sensor, as well as a reference electrode 41, are located adjacent to a first chamber 43 of the assembly, while the remaining sensors are located adjacent to a second chamber 45.

Three stainless steel sleeves 47a, 47b and 47c are positioned at the entrance to the first chamber 43, between the first chamber and the second chamber 45, and at the exit of the second chamber, respectively. The sleeves are arranged to come into direct contact with the adjacent fluid, and the sleeves 47a and 47b are shorted together. The sleeves serve several functions. First, the three sleeves all form part of an hematocrit sensor, which operates by measuring the electrical conductivity of the fluid between the sleeve 47b and the sleeve 47c. Second, the sleeves 47a and 47b are connected to an isolated electrical ground, to protect the patient 11 from electrical shock. Third, the three sleeves all form part of a noise-reduction circuit (not shown in the drawings) that seeks to eliminate electrical currents from traveling along the catheter 21 and infusion tube 17, which otherwise could lead to interference with the signals produced by the various sensors 27–39. An example of such a noise-reduction circuit is disclosed in U.S. Pat. No. 5,220,920.

As the reversible infusion pump 13 draws a blood sample from the patient 11, the blood first comes into sensing contact with the carbon dioxide sensor 27 and, shortly thereafter, with the calcium sensor 35. When the blood sample reaches the carbon dioxide sensor, the signal that is produced begins to increase, because blood ordinarily carries substantially more dissolved carbon dioxide than does the saline solution infusion fluid. When the analyzer 25 detects a rise in the signal from the carbon dioxide sensor to a level in the range of 5 to 15 millivolts above its baseline level, a timer is activated.

After activation of the timer, the analyzer 25 begins monitoring the signal produced by the calcium sensor 35. That signal should show a similar rise above its baseline level within seven to ten seconds after activation of the timer. This is because blood ordinarily carries substantially more ionized calcium than does the infusion fluid being used. If the expected rise in the calcium sensor signal does in fact occur within this time period, it is concluded that the blood sample has reached both the carbon dioxide sensor 27 and the calcium sensor 35.

After the analyzer has detected a rise in the level of the signal from the calcium sensor 35, the controller 23 continues to operate the infusion pump 13 in the rearward direction for a time sufficient to draw about an additional 0.1 to 1.0 milliliters of blood from the patient 11. The internal construction of the sensor assembly 19 is such that the leading edge of the blood sample thereby is drawn nearly all of the way up the length of the tubing 49 located within the assembly housing. In this position, the blood sample should be in sensing contact with all of the assembly's remaining analytical sensors 27-39. The leading edge of the drawn blood preferably remains within the assembly housing both for cosmetic reasons and also to avoid undue delays caused by drawing excessive amounts of blood.

At the point where the prescribed additional amount of blood has been drawn from the patient 11, readings can be taken from any or all of the analytical sensors 27-39. The analyzer 25 reads the various signals from these sensors and converts them into indications of conditions of the patient's blood chemistry. The analyzer may then communicate these blood conditions to the caregiver via a printed record, an optical display, digital data transmission, or any other suitable means.

The blood chemistry system of the invention may also include safety/alarm features that alert the caregiver if a fault or other failure condition is detected. For example, if a predetermined maximum time period elapses after reversal of the infusion pump 13 without the analyzer 25 detecting the expected rise in the signals from the carbon dioxide sensor 27 and/or the calcium sensor 35, it is determined that a failure condition is present. This could be due, for example, to an obstruction in the line or a failure of one or both of the sensors. When this occurs, the controller 23 ceases operating the pump and activates an alarm 50 (FIG. 1), to alert the caregiver. Further, if after reversing the pump a substantial sudden change is noted in the signals from the carbon dioxide sensor and/or the calcium sensor, it is determined that an air bubble might be present in the line. Again, when this occurs, the controller ceases operating the pump, and actuates the alarm, to alert the caregiver.

With reference now to FIG. 3, there is shown a second embodiment of a blood chemistry sensor assembly 19' suitable for incorporation into the system of the invention. This sensor assembly is depicted to include just a single analytical sensor 51, i.e., a glucose sensor. It produces an electrical signal indicative of the concentration of glucose in whatever fluid is located adjacent to it. The sensor is located adjacent to a single chamber 53 of the assembly. Stainless steel sleeves 55a and 55b are located at the chamber's inlet and outlet, respectively, for use in sensing the arrival of a drawn blood sample. As was the case with the stainless steel sleeves 47a, 47b and 47c in the sensor assembly 19 of FIG. 2, these sleeves 55a and 55b also can be used to provide an isolated electrical ground, for shock prevention, and to form electrodes used in a noise-reduction circuit. Such a noise reduction circuit is disclosed in U.S. Pat. No. 5,220,920.

In the sensor assembly 19' of FIG. 3, the analyzer 25 detects the arrival of a drawn blood sample at the site of the chamber 53 by monitoring the electrical conductivity of the fluid between the two stainless steel sleeves 55a and 55b. Such arrival is deduced when the conductivity is detected to exceed a prescribed threshold. An additional blood volume of about 0.4 milliliters then in drawn, to minimize the dilution effects of the adjacent infusion fluid. The leading edge of the blood sample thereby is drawn nearly all of the way up the length of the tubing 57 located within the assembly housing. Additional tubing length is provided by wrapping the tubing around a pair of spaced spools 59a and 59b.

It should be appreciated from the foregoing description that the present invention provides an improved system for monitoring a patient's blood chemistry, which intermittently draws blood samples from the patient into a special sensor assembly having a number of sensors, each sensitive to a particular parameter. After signals produced by these various sensors have been read, the system reinfuses the blood samples back into the patient. Withdrawal of the successive samples into a desired, optimal position within the sensor assembly is achieved by monitoring signals produced by one or more of the analytical sensors, themselves. This allows the infusion tube and catheter to have variable lengths and internal volumes and obviates the need for a separate sensor for detecting the arrival of the blood sample at the desired position.

Preferred embodiments of a fluid infusion and blood testing system incorporating the invention have been described in detail for purposes of understanding and illustration. Various additions and modifications will no doubt occur to those skilled in the art. For example, the layout, number, and type of sensors used may be varied considerably. Other modifications may be made as well without departing from the principles of the invention. Therefore, the scope of the invention should be determined primarily with reference to the appended claims, along with the full scope of equivalents to which those claims are legally entitled.

We claim:

1. A method for monitoring a predetermined parameter of a patient's blood while infusing an infusion fluid through a sensor assembly and catheter into the patient, the method comprising:

operating an infusion pump in a forward direction, to infuse the infusion fluid through the sensor assembly and catheter into the patient;

interrupting infusion of the infusion fluid into the patient by operating the infusion pump in a reverse direction, to draw a blood sample from the patient through the catheter and into the sensor assembly;

monitoring a signal produced by a first sensor of the sensor assembly and detecting a change in the signal indicative of the arrival of the blood sample at the first sensor;

ceasing operation of the infusion pump in the reverse direction in response to detecting the arrival of the blood sample at the first sensor; and monitoring the first sensor signal while the blood sample is in sensing contact with the first sensor, to produce a measurement of a predetermined parameter of the patient's blood.

2. A method as defined in claim 1, and further comprising again operating the infusion pump in the forward direction, to flush the blood sample from sensing contact with the first sensor back through the catheter and into the patient.

3. A method as defined in claim 2, and further comprising intermittently repeating the steps of operating, interrupting, monitoring, ceasing, monitoring, and again operating.

4. A method as defined in claim 1, wherein the first sensor, which produces the signal used in the steps of monitoring, is selected from the group consisting of a carbon dioxide sensor, an oxygen sensor, a potassium sensor, an hematocrit sensor, a calcium sensor, and a sodium sensor.

5. A method as defined in claim 4, wherein:

the sensor assembly includes a carbon dioxide sensor and a calcium sensor; and the step of ceasing operation of the infusion pump in the reverse direction includes ceasing operation of the infusion pump in the reverse direction in response to a predetermined combination of a first signal generated by the carbon dioxide sensor and a second signal generated by the calcium sensor.

6. A method as defined in claim 1, wherein the first sensor, which produces the signal used in the steps of monitoring, is selected from the group consisting of an hematocrit sensor, a temperature sensor, and a pH sensor.

7. A method as defined in claim 1, and further comprising actuating an alarm in response to a predetermined signal from the first sensor.

8. A method as defined in claim 1, and further comprising actuating an alarm in response to the absence of a predetermined signal from the first sensor within a predetermined time period following initiation of the step of interrupting infusion of the infusion fluid.

9. A method as defined in claim 1, wherein ceasing operation of the infusion pump in the reverse direction occurs at a prescribed time after detecting the arrival of the blood sample at the first sensor.

10. A method as defined in claim 1, wherein ceasing operation of the infusion pump in the reverse direction occurs after a prescribed additional volume of blood has been drawn from the patient following the detecting of the arrival of the blood sample at the first sensor.

11. A method as defined in claim 1, wherein:
the sensor assembly includes a plurality of sensors in addition to the first sensor, each of the additional sensors producing a signal indicative of a different predetermined parameter of the adjacent fluid; and
the method further comprises monitoring the signals produced by the plurality of sensors of the sensor assembly, while the blood sample is in sensing contact with the sensors, to produce measurements of a plurality of different predetermined parameters of the patient's blood.

12. A method for monitoring a predetermined parameter of a patient's blood while infusing an infusion fluid through a sensor assembly and catheter into the patient, the method comprising:
operating an infusion pump in a forward direction, to infuse the infusion fluid through the sensor assembly and catheter into the patient;
interrupting infusion of the infusion fluid into the patient by operating the infusion pump in a reverse direction, to draw a blood sample from the patient through the catheter and into the sensor assembly;
monitoring signals produced by first and second sensors of the sensor assembly and detecting changes in the signals indicative of the arrival of the blood sample at the first and second sensors;
ceasing operation of the infusion pump in the reverse direction in a prescribed manner after detecting the arrival of the blood sample at the first and second sensors and
monitoring the signals produced by the first and second sensors of the sensor assembly, while the blood sample is in sensing contact with such sensors, to produce measurements of first and second predetermined parameters of the patient's blood.

13. A method as defined in claim 12, and further comprising again operating the infusion pump in the forward direction, to flush the blood sample from sensing contact with the first and second sensors back into the patient.

14. A method as defined in claim 13, and further comprising intermittently repeating the steps of operating, interrupting, monitoring, ceasing, monitoring, and again operating.

15. A method as defined in claim 12, wherein the first sensor, which produces a signal used in the first step of monitoring, is selected from the group consisting of a carbon dioxide sensor, an oxygen sensor, a potassium sensor, a calcium sensor, and a sodium sensor.

16. A method as defined in claim 15, wherein:
the first sensor of the sensor assembly is a carbon dioxide sensor;
the second sensor of the blood chemistry sensor assembly is a calcium sensor; and
the step of ceasing operation of the infusion pump in the reverse direction includes ceasing operation of the infusion pump in the reverse direction in response to a predetermined combination of a first signal generated by the carbon dioxide sensor and a second signal generated by the calcium sensor.

17. A method as defined in claim 12, wherein the first sensor, which produces a signal used in the first step of monitoring, is selected from the group consisting of an hematocrit sensor, a temperature sensor, and a pH sensor.

18. A method as defined in claim 12, and further comprising actuating an alarm in response to a predetermined signal from the first sensor.

19. A method as defined in claim 12, and further comprising actuating an alarm in response to the absence of a predetermined signal from the first sensor within a predetermined time period following the step of interrupting infusion of the infusion fluid.

20. A method as defined in claim 12, wherein ceasing operation of the infusion pump in the reverse direction occurs after a prescribed additional volume of blood has been drawn from the patient following the detecting of the arrival of the blood sample at the first sensor.

21. A method as defined in claim 12, wherein:
the sensor assembly includes a plurality of sensors, in addition to the first and second sensors, each additional sensor producing a signal indicative of a different predetermined parameter of the adjacent fluid; and
the method further comprises monitoring the signals produced by the plurality of additional sensors of the sensor assembly, while the blood sample is in sensing contact with such additional sensors, to produce measurements of a plurality of different predetermined parameters of the patient's blood.

22. Apparatus for monitoring a predetermined parameter of a patient's blood while infusing an infusion fluid into the patient, comprising:
an infusion line and a catheter configured for insertion into a blood vessel of the patient;
a reversible infusion pump connected between a source of an infusion fluid and the infusion line and catheter;
a blood chemistry sensor assembly mounted in fluid communication with the infusion line and including a first sensor that provides a signal indicative of a predetermined parameter of any fluid present in the infusion line; and
a controller that operates the infusion pump in a forward direction, to pump the infusion fluid through the infusion line and catheter for infusion into the patient, and that intermittently interrupts its operating of the infusion pump in the forward direction to operate the infusion pump in a rearward direction, to draw a blood sample from the patient through the catheter and infusion line into sensing contact with the first sensor of the blood chemistry sensor assembly;
wherein the controller further is configured to monitor the signal provided by the first sensor of the blood chemistry sensor assembly and to detect a change in the signal indicative of the arrival of the blood sample at the first sensor;

wherein the controller, in response to detecting the arrival of the blood sample at the first sensor, ceases its operating of the infusion pump in the rearward direction;

and wherein the signal produced by the first sensor provides an indication of a predetermined parameter of the patient's blood when the blood sample is in sensing contact with the first sensor.

23. Apparatus as defined in claim 22, wherein the first sensor of the blood chemistry sensor assembly is selected from the group consisting of a carbon dioxide sensor, an oxygen sensor, a potassium sensor, a calcium sensor, an hematocrit sensor, and a sodium sensor.

24. Apparatus as defined in claim 23, wherein the the first sensor of the blood chemistry sensor assembly is a carbon dioxide sensor;

the blood chemistry sensor assembly further includes a calcium sensor; and the controller is configured to detect the arrival of the blood sample at the first sensor in response to a predetermined combination of a first signal generated by the carbon dioxide sensor and a second signal generated by the calcium sensor.

25. Apparatus as defined in claim 22, wherein the first sensor of the blood chemistry sensor assembly is selected from the group consisting of an hematocrit sensor, a temperature sensor, and a pH sensor.

26. Apparatus as defined in claim 22, and further comprising an alarm actuatable in response to a predetermined signal from the first sensor.

27. Apparatus as defined in claim 22, and further comprising an alarm actuatable in response to the absence of a predetermined signal from the first sensor of the blood chemistry sensor assembly within a predetermined time period after the controller initiates its operating of the infusion pump in the reverse direction.

28. Apparatus as defined in claim 22, wherein the controller is configured to cease its operating of the infusion in the reverse direction at a prescribed time after detecting the arrival of the blood sample at the first sensor of the blood chemistry sensor assembly.

29. Apparatus as defined in claim 22, wherein the controller is configured to cease its operating of the infusion pump in the reverse direction after a prescribed additional volume of blood has been drawn from the patient following the detecting of the arrival of the blood sample at the first sensor of the blood chemistry sensor assembly.

30. Apparatus as defined in claim 22, wherein:

the blood chemistry sensor assembly further includes a plurality of sensors in addition to the first sensor, each of the additional sensors producing a signal indicative of a different predetermined parameter of the adjacent fluid; and the apparatus further comprises a monitor that monitors the signals produced by the plurality of sensors of the sensor assembly, while the blood sample is in sensing contact with the sensors, to produce measurements of a plurality of different predetermined parameters of the patient's blood.

31. Apparatus for monitoring a predetermined parameter of patient's blood while infusing an infusion fluid into the patient, comprising:

an infusion line and a catheter configured for insertion into a blood vessel of the patient;

a reversible infusion pump connected between a source of an infusion fluid and the infusion line and catheter;

a blood chemistry senior assembly mounted in flow communication with the infusion line and including first and second sensors that each provide a signal indicative of a different predetermined parameter of any fluid present un the infusion line; and a controller that operates the infusion pump in a forward direction, to pump the infusion fluid through the infusion line and catheter for infusion into the patient, and that intermittently interrupts its operating of the infusion pump in the forward direction to operate the infusion pump in a rearward direction, to draw a blood sample from the patient through the catheter and infusion line into sensing contact with the first and second sensors of the blood chemistry sensor assembly;

wherein the controller further is configured to monitor the signals provided by the first and second sensors of the blood chemistry sensor assembly and to detect changes in the signals indicative of the arrival of the blood sample at the first and second sensors;

wherein the controller ceases its operating of the infusion pump in the rearward direction in a prescribed manner after detecting the arrival of the blood sample at the first and second sensors and the controller thereafter resumes its operating of the pump in the forward direction, to reinfuse the drawn blood sample back into the patient via the infusion tube and catheter;

and wherein the signal produced by the first sensor provides an indication of a predetermined parameter of the patient's blood when the blood sample is in sensing contact with the first sensor.

32. Apparatus as defined in claim 31, wherein the first sensor of the blood chemistry sensor assembly is selected from the group consisting of a carbon dioxide sensor, an oxygen sensor, a potassium sensor, a calcium sensor, an hematocrit sensor, and a sodium sensor.

33. Apparatus as defined in claim 32, wherein;

the first sensor of blood chemistry sensor assembly is a carbon dioxide sensor;

the second sensor of the blood chemistry sensor assembly is a calcium sensor; and the controller is configured to detect the arrival of the blood sample at the first and second sensors in response to a predetermined combination of a first signal generated by the carbon dioxide sensor and a second signal generated by the calcium sensor.

34. Apparatus as defined in claim 31, wherein the first sensor of the blood chemistry sensor assembly is selected from the group consisting of an hematocrit sensor, a temperature sensor, and a pH sensor.

35. Apparatus as defined in claim 31, and further comprising an alarm actuatable in response to a predetermined signal from the first sensor.

36. Apparatus as defined in claim 31, and further comprising an alarm actuatable in response to the absence of a predetermined signal from the first sensor of the blood chemistry sensor assembly within a predetermined time period after the controller initiates its operating of the infusion pump in the reverse direction.

37. Apparatus as defined in claim 31, wherein the controller is configured to cease its operating of the infusion pump in the reverse direction after a prescribed additional volume of blood has been drawn from the patient following the detecting of the arrival of the blood sample at the first and second sensors of the blood chemistry sensor assembly.

38. Apparatus as defined in claim 31, wherein:

the blood chemistry sensor assembly further includes a plurality of sensors in addition to the first and second sensors, each of the additional sensors producing a signal indicative of a different predetermined parameter of the adjacent fluid; and the apparatus further comprises a monitor that monitors the signals produced by the plurality of sensors of the sensor assembly, while the blood sample is in sensing contact with the sensors, to produce measurements of a plurality of different predetermined parameters of the patient's blood.

* * * * *